United States Patent
Lutz et al.

(10) Patent No.: US 10,779,871 B2
(45) Date of Patent: Sep. 22, 2020

(54) FLEXIBLE SURGICAL SCREW DRIVER

(71) Applicant: SWEMAC INNOVATION AB, Linköping (SE)

(72) Inventors: Christian Lutz, Heikendorf (DE); Klaus Dorawa, Schönkirchen (DE)

(73) Assignee: SWEMAC INNOVATION AB, Linkoping (SE)

( * ) Notice: Subject to any disclaimer, the term of this patent is extended or adjusted under 35 U.S.C. 154(b) by 333 days.

(21) Appl. No.: 15/527,118

(22) PCT Filed: Nov. 25, 2014

(86) PCT No.: PCT/EP2014/075530
§ 371 (c)(1),
(2) Date: May 16, 2017

(87) PCT Pub. No.: WO2016/082864
PCT Pub. Date: Jun. 2, 2016

(65) Prior Publication Data
US 2019/0090926 A1    Mar. 28, 2019

(51) Int. Cl.
*A61B 17/88* (2006.01)
*A61B 17/16* (2006.01)
(Continued)

(52) U.S. Cl.
CPC ...... *A61B 17/8875* (2013.01); *A61B 17/1631* (2013.01); *A61B 17/808* (2013.01); *B25B 15/00* (2013.01); *B25B 23/0042* (2013.01)

(58) Field of Classification Search
CPC ............ A61B 17/8875; A61B 17/1631; A61B 17/1613; A61B 17/808; A61B 17/8872;
(Continued)

(56) References Cited

U.S. PATENT DOCUMENTS

| 4,876,929 | A | * | 10/1989 | Kozak | B25B 13/481 |
| | | | | | 81/57.43 |
| 5,464,407 | A | * | 11/1995 | McGuire | A61B 17/15 |
| | | | | | 606/104 |

(Continued)

FOREIGN PATENT DOCUMENTS

| JP | 55-045489 | 9/1953 |
| JP | 08-108375 | 4/1996 |

(Continued)

*Primary Examiner* — David W Bates
*Assistant Examiner* — Marcela I Shirsat
(74) *Attorney, Agent, or Firm* — Tarolli, Sundheim, Covell & Tummino LLP

(57) ABSTRACT

A flexible surgical screw driver comprises a rotatable handle member, a shaft member and a flexible member. The handle member is configured with a first coupling means and the shaft member with a second coupling means. These first and second coupling means are configured to cooperate such that the handle member and the shaft member are angularly displaceable relative to each other and such that said handle member and said shaft member are non-rotatably coupled to each other for driving a screw with rotation transmitted from the handle member. The flexible member is configured to connect the handle member and the shaft member to each other and hold said handle member and said shaft member together such that the longitudinal axes thereof are substantially aligned and such that angular displacement of the handle member and the shaft member relative to each other such that the longitudinal axes thereof are misaligned, can be performed against the action of said flexible member.

20 Claims, 3 Drawing Sheets

(51) Int. Cl.
*B25B 15/00* (2006.01)
*B25B 23/00* (2006.01)
*A61B 17/80* (2006.01)

(58) Field of Classification Search
CPC ....... B25B 13/481; B25B 15/00; B25B 15/02; B25B 23/0007; B25B 23/0042; B25B 23/0014
USPC ... 81/52, 53.1, 478, 57.26, 57.27, 57.43, 64, 81/177.6; 606/104
See application file for complete search history.

(56) References Cited

U.S. PATENT DOCUMENTS

| | | | | |
|---|---|---|---|---|
| 5,638,726 | A | * | 6/1997 | Pelkonen .............. B25B 13/481 |
| | | | | 81/177.2 |
| 6,827,722 | B1 | * | 12/2004 | Schoenefeld ...... A61B 17/1622 |
| | | | | 606/104 |
| 2010/0064860 | A1 | * | 3/2010 | Kozak ................ B25B 23/0028 |
| | | | | 81/177.6 |
| 2011/0152867 | A1 | | 6/2011 | Petrezelka et al. |
| 2012/0109142 | A1 | * | 5/2012 | Dayan ................ A61B 17/8888 |
| | | | | 606/104 |
| 2012/0143195 | A1 | * | 6/2012 | Sander ................ A61B 17/162 |
| | | | | 606/80 |

FOREIGN PATENT DOCUMENTS

| | | |
|---|---|---|
| JP | 08-206128 | 8/1996 |
| JP | 2006-525061 | 11/2006 |

* cited by examiner

FLEXIBLE SURGICAL SCREW DRIVER

RELATED APPLICATION

This application corresponds to PCT/EP2014/075530, filed Nov. 25, 2014, the subject matter, of which is incorporated herein by reference in its entirety.

TECHNICAL FIELD

The present invention relates to a flexible surgical screw driver. The screw driver comprises a rotatable handle member, a shaft member and a flexible member. The handle member is configured with a first coupling means on a distal portion thereof. The shaft member is configured with a drive tip on a distal portion thereof and with a second coupling means on a proximal portion thereof. The first and second coupling means are configured to co-operate for permitting angular displacement of the handle member and the shaft member relative to each other and for transmitting torque from the handle member to the shaft member.

BACKGROUND OF THE INVENTION

Flexible surgical screw drivers are already known in the prior art.

Thus, one type of prior art flexible screw driver uses a universal joint as coupling means to achieve angular displacement or angulation of the shaft member relative to the handle member and for transmitting torque from the handle member to the shaft member. The universal joint has two major disadvantages. First, it is very bulky. It needs much space, it is too big for easy positioning of the screw driver in correct location for use and it obstructs the view for the surgeon. Secondly, the universal joint is not sufficiently constrained. In fact, it is fully non-constrained, resulting in that the drive tip of the screw driver is swiveling free in all directions and cannot be directed or controlled to get to a specific target such as a screw.

A second type of prior art flexible screw driver uses a coif to permit angular displacement of the shaft member relative to the handle member and to permit torque transmission. This type of flexible screw driver permits direction of the drive tip of the screw driver towards a specific target. On the other hand, the coil is for natural reasons configured such that it opens and closes, allowing body fluids to enter the coil and the coil is difficult, if not impossible, to clean. Secondly, although it is possible to direct the drive tip of the screw driver towards a specific target, the coil has a preferred direction, i.e. depending on in which direction the coil has its pitch, left or right, it can transfer more or less torque. Rotation in the preferred direction will close the windings of the coil and more torque can be transmitted. Rotation in the opposite direction will open the windings of the coil and less torque can be transmitted.

Both prior art types of flexible surgical screw drivers have in common that the coupling means are configured in an attempt to fulfill two functions at the same time, namely for permitting angular displacement of the handle member and the shaft member relative to each other and for transmitting torque from the handle member to the shaft member. The result is that the prior art cannot provide a flexible surgical screw driver wherein these two functions are combined in a satisfactory manner.

SUMMARY OF THE INVENTION

The primary object of the present invention is to overcome or at least ameliorate the disadvantages of the prior art by improving the flexible surgical screw driver such that angular displacement of the rotatable handle member and the shaft member relative to each other can be performed with ease in order to reach and engage a target which is difficult to access and operate, that torque nevertheless at the same time can be transmitted from the handle member to the shaft member in a safe and effective manner without any loss thereof and that after having performed the intended operation, the angular displacement of the shaft member relative to the handle member is automatically reversed.

This is arrived at according to the invention by configuring the flexible surgical screw driver with the above-mentioned rotatable handle member and the shaft member and by configuring the first and second coupling means of the handle member and the shaft member respectively, to cooperate such that said handle member and said shaft member are angularly displaceable relative to each other and such that said handle member and said shaft member are non-rotatably coupled to each other for driving a screw with rotation transmitted from the handle member. The primary object of the invention is also arrived at by configuring the flexible surgical screw driver also with the above-mentioned separate flexible member, which in turn is configured such that said flexible member connects the handle member and the shaft member to each other and holds said handle member and said shaft member together such that the longitudinal axes thereof are substantially aligned and such that angular displacement of the handle member and the shaft member relative to each other such that the longitudinal axes thereof are misaligned, can be performed against the action of said flexible member.

Thus, in a primary aspect of the present invention, there is provided a flexible surgical screw driver which, when not in use, by means of the flexible member permits precise and easy direction and connection of the screw driver to a target such as a screw and which allows angular displacement by bringing the drive tip of the screw driver to engage the screw head and then, thanks to the coupling means, reposition the rotatable handle member relative to the shaft member against the action of the flexible member such that said handle member attains a position where it is easy to grip for rotation. Thanks to the coupling means, which are non-rotatably coupled to each other, torque can now be transmitted effectively from the handle member to the shaft member such that the shaft member is rotated for driving the screw with rotation. Finally, after securing of the screw and removal of the drive tip of the screw driver from the screw and while still holding the screw driver, the action of the flexible member returns the shaft member to its inoperative position relative to the handle member, with the longitudinal axes of said members in substantial alignment with each other.

Preferred embodiments of the flexible surgical screw driver according to the invention and features thereof are defined in the dependent claims.

BRIEF DESCRIPTION OF THE DRAWINGS

The present invention will hereinafter be further explained by means of non-limiting examples with reference to the accompanying drawings, in which.

It should be noted that the accompanying drawings are not necessarily drawn to scale and that the dimensions of some features of the present invention may have been exaggerated for the sake of clarity.

DETAILED DESCRIPTION OF PREFERRED EMBODIMENTS

The present invention will in the following be exemplified by embodiments. It should however be realized that the embodiments are included to explain principles of the invention and not to limit the scope of the invention as defined in the appended claims. Details from the embodiments may be combined with each other.

Figure 1:
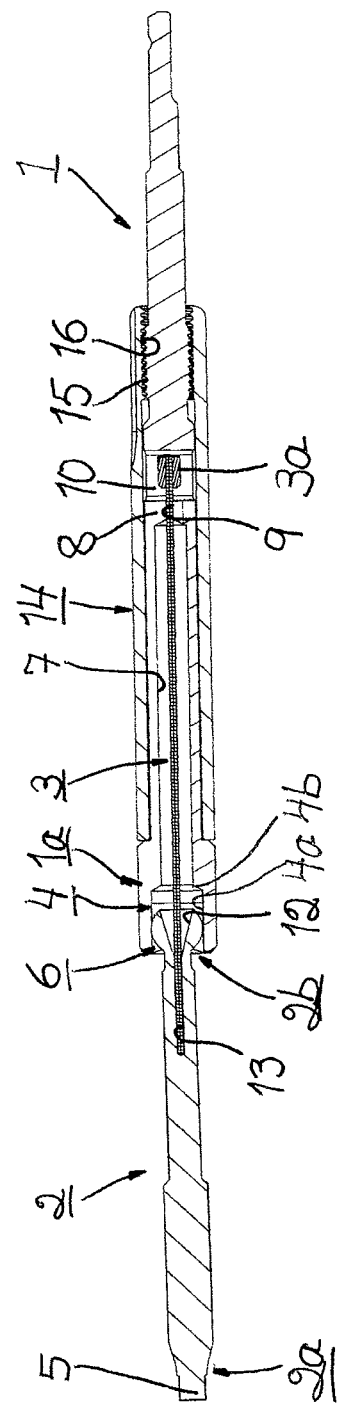
FIG. 1 is a schematic sectional view of a first embodiment of the flexible surgical screw driver according to the invention in inoperative position.
Figure 2:
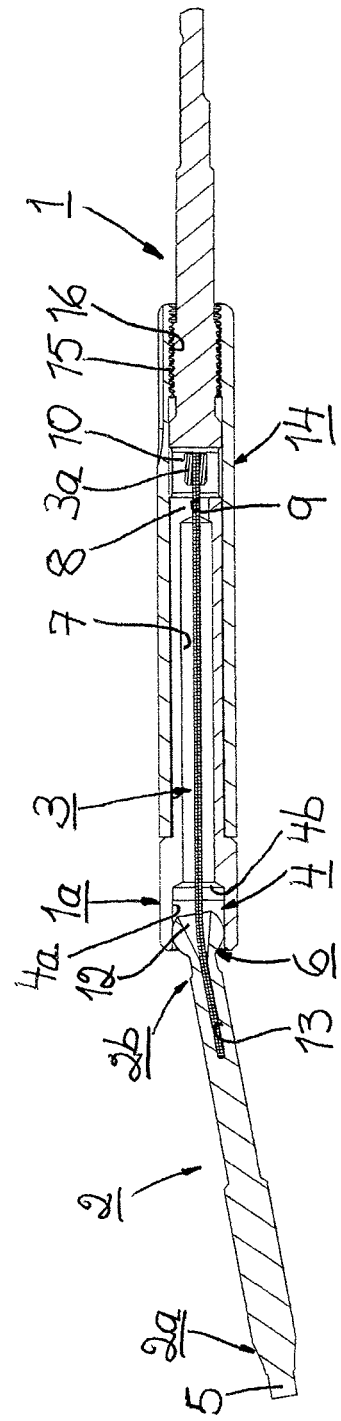
FIG. 2 is a schematic sectional view of the flexible surgical screw driver of FIG. 1 in an operative position.

FIGS. 1 and 2 illustrate as mentioned a preferred first embodiment of the flexible surgical screw driver according to the present invention. This flexible surgical screw driver comprises a rotatable handle member 1, a shaft member 2 and a flexible member 3.

The rotatable handle member 1 is configured with a first coupling means 4. This first coupling means 4 is located on a distal end portion 1a of the handle member 1. The shaft member 2 is configured with a drive tip 5. The drive tip is located on a distal end portion 2a of the shaft member 2. The shaft member 2 is also configured with a second coupling means 6. This second coupling means 6 is found on a proximal end portion 2b of the shaft member 2.

The first and second coupling means 4, 6 are configured to cooperate with each other such that the rotatable handle member 1 and the shaft member 2 will interact as desired according to the present invention.

Thus, the first and second coupling means 4, 6 are configured to cooperate such that the rotatable handle member 1 and the shaft member 2 are angularly displaceable relative to each other. Thereby, when a target in the form of e.g. a screw is located such that it will be difficult to secure it with an ordinary screw driver, it is by means of the flexible surgical screw driver according to the present invention possible to first engage the head of the screw (not illustrated) with the drive tip 5 on the shaft member 2 and then reposition the handle member 1 relative to the shaft member such that said handle member can attain a position where it is easy to maintain the grip around the handle member for safe and effective driving and securing of the screw.

Accordingly, the first and second coupling means 4, 6 are also configured to cooperate such that the rotatable handle member 1 and the shaft member 2 are non-rotatably connected to each other for driving the screw with rotation transmitted from the handle member. The handle member 1 is held and rotated preferably by hand and the rotary motion is transferred from the handle member to the shaft member 2 by means of the non-rotatable connection between said members such that the drive tip 5 on the shaft member, engaging the head of the screw, rotates the screw with sufficient torque for driving and securing thereof.

The first and second coupling means 4, 6 are of course configured such that the non-rotatable connection between the rotatable handle member 1 and the shaft member 2 is maintained irrespective of whether said members are angularly displaced relative to each other or not, i.e. the flexible surgical screw driver according to the present invention functions also as an ordinary screw driver.

The flexible member 3 is according to the invention configured to connect the rotatable handle member 1 and the shaft member 2 to each other and to hold said members together. This connection and holding together is realized by means of said flexible member 3 such that the longitudinal axes of the handle member 1 and the shaft member 2 are substantially aligned when the flexible surgical screw driver is not in use, i.e. in inoperative position. It is also realized by means of said flexible member 3 such that angular displacement of the handle member 1 and the shaft member 2 relative to each other such that the longitudinal axes of said members are misaligned, can be performed against the action of the flexible member 3 when the flexible surgical screw driver is in use, i.e. in operative position with the drive tip 5 of the shaft member engaging the head of a screw for driving the screw and securing it in position. After securing of the screw and removal of the drive tip 5 of the shaft member 2 therefrom, the flexible member 3 returns the shaft member to its inoperative position relative to the handle member 1, with the longitudinal axes of said members in substantial alignment with each other.

The flexible surgical screw driver according to the present invention provides for equal torque transmission in both directions of rotation. By means of the flexible member 3, it has a basic stiffness and it is thereby also easy to permit precise and easy direction of the flexible surgical screw driver towards the head of a screw and easy connection of the screw driver to the screw. The screw driver stays straight until a bending moment is applied thereto.

In the embodiment of FIGS. 1 and 2, the first coupling means on the distal end portion 1a of the rotatable handle member 1 is configured as a recess 4. The second coupling means on the proximal end portion 2b of the shaft member 2 is configured as a ball head 6 which is non-rotatably received in the recess 4. The configuration as a ball head permits in a simple manner said angular displacement of the handle member 1 and the shaft member 2 relative to each other. The ball head 6 has in the illustrated embodiment according to FIGS. 1 and 2 as well as according to FIG. 3, in cross section, an external hexagonal shape and the recess 4 a corresponding internal hexagonal shape. The hexagonal shape provides in a simple manner for said non-rotatable connection of the handle member 1 and the shaft member 2 to each other.

Alternatively, instead of the recess 4 and the ball head 6, an angle gear drive can be used as first and second coupling means 4, 6.

In the embodiment of FIGS. 1 and 2, the recess 4 in the distal end portion 1a of the rotatable handle member 1 comprises a distal portion 4a for receiving the ball head 6 and a short proximal portion 4b which is tapering conically towards the proximal end of the handle member. The recess 4 continues proximally as an elongate recess 7 having a smaller diameter than the distal recess and which extends in the longitudinal direction of the handle member 1. The proximal portion 4b of the recess 4 has the conically tapering shape to avoid sharp edges which can damage the flexible member 3 where said recess transforms into the smaller diameter elongate recess 7. Also, the diameter of the elongate recess 7 is relatively much larger than the diameter of the flexible member 3 in order to give room for the flexible member to flex. The smaller diameter elongate recess 7 ends as illustrated in FIGS. 1 and 2 at a partition wall 8 which has an even smaller diameter hole 9 therein. The proximal end of the hole 9 opens into a larger diameter proximal recess 10 in the handle member 1. The proximal recess 10 has a diameter which is substantially the same as the diameter of the distal portion 4a of the distal recess 4. The larger diameter proximal recess 10 may be located as illustrated in FIGS. 1 and 2 or it may be located in the proximal end portion 1b of the handle member 1 or in any other suitable position along the handle member.

Figure 3:
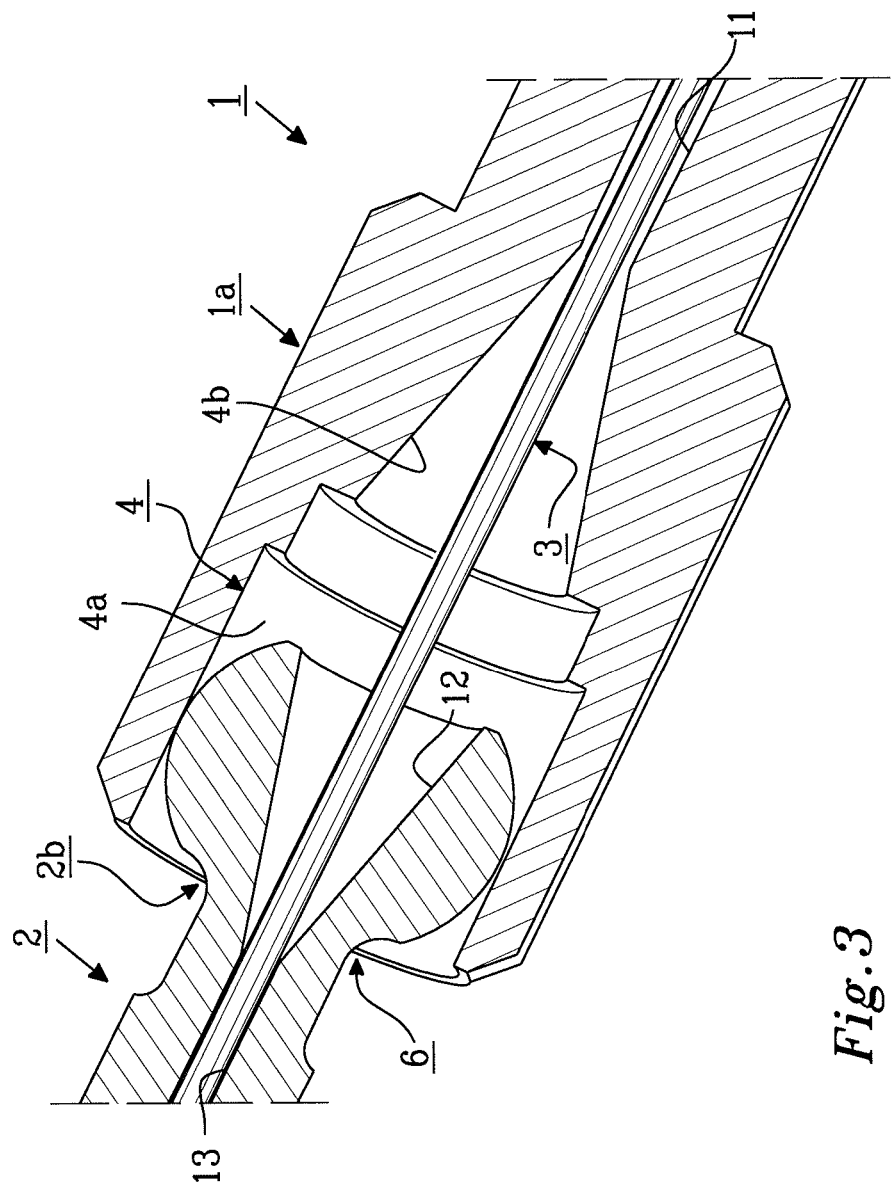
FIG. 3 is an enlarged schematic sectional view of the portions provided with coupling means of the rotatable handle member and the shaft member of a second embodiment of the flexible surgical screw driver according to the invention in inoperative position.

In the alternative illustrated in FIG. 3, the recess 4 in the distal end portion 1a of the rotatable handle member 1 also comprises a distal portion 4a for receiving the ball head 6 and a proximal portion 4b which is tapering conically towards the proximal end of the handle member. The taper may vary, but is here nevertheless much longer than the conically tapering proximal portion 4b of the recess in the embodiment of FIGS. 1 and 2. The purpose of the tapering portion 4b is the same as for the tapering proximal portion 4b of the recess 4 in the embodiment of FIGS. 1 and 2, i.e. to avoid sharp edges which can damage the flexible member 3. The tapering proximal portion 4b of the recess 4 continues proximally as a passage 11 having a smaller diameter than the distal recess and which extends in the longitudinal direction of the handle member 1. Contrary to the smaller diameter elongate recess 7 in the embodiment of FIGS. 1 and 2, the diameter of this smaller diameter passage 11 is only somewhat larger than the diameter of the flexible member 3. Thereby, no partition wall with a hole therein is needed. Instead, the smaller diameter passage 11 ends proximally directly with a larger diameter proximal recess similar to the proximal recess 10 in the embodiment of FIGS. 1 and 2. This proximal recess may be located as in the embodiment of FIGS. 1 and 2 or it may be located in the proximal end portion of the handle member 1 or in any other suitable position along the handle member.

The ball head 6 on the proximal end portion 2b of the shaft member 2 is configured with a recess 12 which is tapering towards the distal end portion 2a of the shaft member. The purpose of the tapering recess 12 is the same as for the conical proximal part of the recess 4 in the embodiment of FIGS. 1 and 2 and for the tapering portion 4b of the same recess in the embodiment of FIG. 3, i.e. to avoid sharp edges which can damage the flexible member 3. The tapering recess 12 continues distally as a smaller diameter passage 13, i.e. the diameter of the passage is smaller than the diameter of the recess. This smaller diameter passage 13 extends in the longitudinal direction of the shaft member 2. The smaller diameter passage 13 ends in the illustrated embodiment of FIGS. 1 and 2 a short distance distally of the recess 12, but may alternatively extend through the entire shaft member 2 and end short of the drive tip 5 at the distal end portion 2a thereof or at any other suitable point along said shaft member.

The flexible member is according to the present invention preferably configured as a spring wire 3 which at its distal end is fixedly attached to the shaft member 2 and which at its proximal end is releasably located in the rotatable handle member 1, as in the embodiment illustrated in FIGS. 1 and 2. Alternatively, the spring wire 3 may be fixedly attached also to the handle member 1. The spring wire 3 must be elastically deformable such that it can be bent and stretched during angular displacement of the handle member 1 and the shaft member 2 relative to each other and such that it can return to its original state and thereby return the handle member and the shaft member to their inoperative position relative to each other when the flexible surgical screw driver is no longer in use. The spring wire 3 may be metallic, e.g. made of steel or nitinol, it may be plastic, e.g. made of silicone, or it may be made of carbon fiber or any other material with the proper elastic properties. The diameter of the spring wire 3 is chosen based on the desired stiffness of the screw driver, i.e. based on the desired force to bring about angular displacement of the handle member 1 and the shaft member 2 relative to each other and the desired spring force for returning said handle member and said shaft member to their inoperative position.

By configuring the flexible member as a spring wire 3, the flexible member has been given the best possible shape for location in the limited space provided in the rotatable handle member 1 and the shaft member 2. Accordingly, the spring wire 3 is configured for fixed attachment in and extension through the smaller diameter passage 13 as well as through the tapering proximal recess 12 in the shaft member 2. The spring wire 3 may be fixedly attached in the shaft member 2 e.g. by spot welding through a lateral hole (not illustrated) in the shaft member or along its entire length by means of a laser, or by a simple press fit in the smaller diameter passage 13 in the shaft member.

In the embodiment of FIGS. 1 and 2, the spring wire 3 is further configured for extension through the distal recess 4, the smaller diameter elongate recess 7 and the hole 9 in the partition wall 8 and into the larger diameter proximal recess 10 in the rotatable handle member 1 for releasable location therein. Alternatively, in the embodiment of FIG. 3, the spring wire 3 is configured for extension through the distal recess 4 and the smaller diameter passage 11 and into the larger diameter proximal recess 10 in the handle member 1 for releasable connection therein. By configuring the proximal end portion of the spring wire 3 with an enlarged part 3a which may be integral with the spring wire or a separate member which is fixedly attached to said proximal end portion of the spring wire, it is possible to achieve the releasable location of said spring wire in the larger diameter proximal recess 10 in the handle member 1 in a simple manner. When angular displacement of the handle member 1 and the shaft member 2 relative to each other occurs and the spring wire 3 is bent and stretched, the enlarged part 3a of the spring wire will move towards and engage the partition wall 8 around the hole 9 therein or it will move towards the distal wall defining the proximal recess 10 in the handle member and engage said distal wall around the opening into the smaller diameter passage 11. Thus, the enlarged part 3a of the spring wire 3 functions as a stop element. The enlarged part 3a of the spring wire may e.g. be a ball or a cylindrical element as in the embodiment of FIGS. 1 and 2. Releasable connection of the spring wire 3 will also ease the tension thereof during bending and stretching.

The flexible surgical screw driver according to the present invention may be used as an ordinary screw driver since the spring force of the as a spring wire configured flexible member 3 is capable of holding the rotatable handle member 1 and the shaft member 2 such that the longitudinal axes thereof are substantially aligned. The first and second coupling means 4, 6 see to that the handle member 1 and the shaft member 2 are non-rotatably connected to each other, such that rotation of the handle member is transmitted from the handle member to the shaft member and from the shaft member to the target, e.g. the screw, such that sufficient torque is provided for driving and securing the screw. However, when a screw is located such that securing thereof cannot be performed by means of an ordinary screw driver and instead, the handle member 1 and the shaft member 2 must be angularly displaced relative to each other for optimum securing of the screw, this will be possible by means of the screw driver described above by bringing the drive tip 5 of the screw driver to engage the head of the screw and then, thanks to the configuration of the coupling means 4, 6, reposition the handle member and the shaft member relative to each other against the action of the flexible member 3, which is bent and stretched, such that said handle member attains a position where it is easy to grip for rotation. The first and second coupling means 4, 6 are configured such that the handle member 1 and the shaft member 2 thereby still are non-rotatably connected to each other, such that rotation of the handle member is transmitted from the handle member to the angularly displaced shaft member and from the shaft member to the screw with sufficient torque for effective driving and securing of the screw. The conically tapering parts 4b and 12 of the handle member 1 and the shaft member 2 respectively, see to that the flexible member 3 is not damaged during the rotation and the smaller diameter parts 7; 11 see to that there is sufficient space for the flexible member to flex if necessary. After securing of the screw and removal of the drive tip 5 of the screw driver from the screw head and while still holding the handle member, the flexible member 3 strives to return to its unbent and unstretched condition. This action of the flexible member 3 brings the shaft member 2 to spring back relative to the handle member 1 such that the longitudinal axis of said shaft member is substantially aligned with the longitudinal axis of said handle mem-ber 1, i.e. the flexible member thereby sees to that the angular displacement of the handle member and the shaft member relative to each other ceases.

For cleaning of the flexible surgical screw driver after use, the rotatable handle member 1 comprises preferably two parts, one of which is illustrated in FIGS. 1 and 2. The two parts are configured such that they when assembled define the recesses 4, 7, 10 for the flexible member, i.e. the spring wire 3, therein. Alternatively, the two parts are configured such that they when assembled define the distal and proximal recesses 4, 10 as well as the intermediate smaller diameter passage 11 for the flexible member, i.e. the spring wire 3, therein. If the flexible member 3 is fixedly attached to the handle member 1, it should be attached only to one part thereof, such that disassembly of the handle member for cleaning is still possible. The two parts are held together by means of a suitable clamping device, e.g. a sleeve 14 which is threaded onto said handle member parts, as in the illustrated embodiment according to FIGS. 1 and 2, which each is configured with an outer threading 15 which correspond with an inner threading 16 of the sleeve. As with the sleeve 14, it is preferred if the clamping device is configured also to be gripped and held by a surgeon when the screw driver is used.

The shaft member 2 comprises on the other hand one, integral part only. This integral part is configured with the recess 12 and the smaller diameter passage 13 for the flexible member, i.e. the spring wire 3.

Further modifications of the present invention within the scope of the appended claims are feasible without departing from the idea and object of the invention. As such, the present invention should not be considered as limited by the embodiments described above or by the figures illustrating these embodiments. Rather, the full scope of the invention should be determined by the appended claims with reference to the description and drawings. Thus, as indicated, the size and shape of the recesses and passages in the rotatable handle member as well as in the shaft member may vary and so may size, shape and construction of the coupling means and the flexible member received in these recesses and passages.

The invention claimed is:

1. Flexible surgical screw driver, comprising:
   a rotatable handle member (1), a shaft member (2) and an internal flexible member (3),
   wherein said handle member (1) is configured with a first coupling means (4) on a distal end portion (1a) thereof,
   wherein said shaft member (2) is configured with a drive tip (5) on a distal end portion (2a) thereof and a second coupling means (6) on a proximal end portion (2b) thereof,
   wherein said first and second coupling means (4, 6) are configured to cooperate such that said handle member (1) and said shaft member (2) are angularly displaceable relative to each other and such that said handle member (1) and said shaft member (2) are non-rotatably coupled to each other for driving a target such as a screw with rotation transmitted from the handle member (1),
   wherein said internal flexible member (3) is an elastically deformable spring wire which extends through one of an elongate recess (7) and an elongate passage (11) in the handle member (1), and through a passage (13) in the shaft member (2) to connect the handle member (1) and the shaft member (2) to each other and bias said handle member (1) and shaft member (2) together such that longitudinal axes of the handle and shaft members (1, 2) are substantially aligned, and
   wherein angular displacement of the handle member (1) and the shaft member (2) relative to each other, which misaligns the longitudinal axes of the handle and shaft members (1, 2), is performed by repositioning the rotatable handle member (1) relative to the shaft member (2) against the bias of the elastically deformable spring wire (3).

2. Flexible surgical screw driver according to claim 1,
   wherein the first coupling means on the distal end portion (1a) of the rotatable handle member (1) is configured as a recess (4), and
   wherein the second coupling means on the proximal end portion (2b) of the shaft member (2) is configured as a ball head (6) which is non-rotatably received in said recess (4).

3. Flexible surgical screw driver according to claim 2, wherein the recess (4) in the distal end portion (1a) of the rotatable handle member (1) comprises a distal portion (4a) for receiving the ball head (6) and a proximal portion (4b) which is tapering towards the proximal end of the handle member (1).

4. Flexible surgical screw driver according to claim 3, wherein the proximal portion (4b) of the recess (4) continues proximally into the elongate recess (7), the elongate recess (7) extending in the longitudinal direction of the handle member (1) and having a diameter that is smaller than a diameter of the distal portion (4a) of the recess (4).

5. Flexible surgical screw drive according to claim 4, wherein the elongate recess (7) ends at a partition wall (8), said partition wall having a hole (9) therein, the proximal end of which opens into a larger diameter proximal recess (10) in the handle member (1), the larger diameter proximal recess (10) having a larger diameter than the diameter of the elongate recess (7).

6. Flexible surgical screw driver according to claim 3, wherein the proximal portion (4b) of the recess (4) continues proximally into the elongate passage (11) of the handle member (1), the elongate passage (11) of the handle member (1) extending in the longitudinal direction of the handle member (1) and having a diameter that is smaller than a diameter of the distal portion (4a) of the recess (4).

7. Flexible surgical screw driver according to claim 6, wherein the elongate passage (11) of the handle member (1) ends proximally with a larger diameter proximal recess (10)

in the handle member (1), the larger diameter proximal recess (10) having a larger diameter than the diameter of the elongate passage (11) of the handle member (1).

8. Flexible surgical screw driver according to claim 2, wherein the ball head (6) on the proximal end portion (2*b*) of the shaft member (2) is configured with a recess (12) which is tapering towards the distal portion of the shaft member (2).

9. Flexible surgical screw driver according to claim 8, wherein the recess (12) in the ball head (6) on the proximal end portion (2*b*) of the shaft member (2) continues distally into the passage (13) in the shaft member (2), the passage (13) extending in the longitudinal direction of the shaft member (2) and having a diameter that is smaller than a diameter of the recess (12).

10. Flexible surgical screw driver according to claim 9, wherein the passage (13) in the shaft member (2) extends toward the drive tip (5) at the distal end portion (2*a*) thereof.

11. Flexible surgical screw driver according to claim 2, wherein the elastically deformable spring wire (3) which at its distal end is fixedly attached to the shaft member (2) and which at its proximal end is releasably located in the handle member (1).

12. Flexible surgical screw driver according to claim 11, wherein
the elongate recess (7) ends at a partition wall (8), said partition wall (8) having a hole (9) therein, the proximal end of which opens into a larger diameter proximal recess (10) in the handle member (1), the larger diameter proximal recess (10) having a larger diameter than a diameter of the elongate recess (7);
the ball head (6) on the proximal end portion (2*b*) of the shaft member (2) is configured with a recess (12) which tapers towards a distal portion of the shaft member (2) and into the passage (13) in the shaft member (2); and
the spring wire (3) is configured for fixed attachment in and extension through the passage (13) in the shaft member (2) as well as through the recess (12) in the shaft member (2) and for extension through the recess (4) in the distal end portion (1*a*) of the handle member (1), the elongate recess (7), and the hole (9) in the partition wall (8) and into the larger diameter proximal recess (10) in the handle member (1) for releasable location therein.

13. Flexible surgical screw driver according to claim 12, wherein the handle member (1) comprises two parts which are configured such that when assembled they define the recesses (4, 7, 10) in the handle member (1) for the spring wire (3) therein and which are held together by means of a sleeve (14).

14. Flexible surgical screw driver according to claim 11, wherein
the elongate passage (11) in the handle member (1) ends proximally with a proximal recess (10) in the handle member (1), the proximal recess (10) having a larger diameter than a diameter of the elongate passage (11) of the handle member (1);
the ball head (6) on the proximal end portion (2*b*) of the shaft member (2) is configured with a recess (12) which tapers towards a distal portion of the shaft member (2) and into the passage (13) in the shaft member (2); and
the spring wire (3) is configured for fixed attachment in and extension through the passage (13) in the shaft member (2) as well as through the recess (12) in the shaft member (2) and for extension through the recess (4) in the distal end portion (1*a*) of the handle member (1) and the elongate passage (11) of the handle member (1) and into the larger diameter proximal recess (10) in the handle member (1) for releasable location therein.

15. Flexible surgical screw driver according to claim 14, wherein the handle member (1) comprises two parts which are configured such that when assembled they define the recesses (4, 10) in the handle member (1) as well as the elongate passage (11) in the handle member (1) for the spring wire (3) therein and which are held together by means of a sleeve (14).

16. Flexible surgical screw driver according to claim 11, wherein a proximal end portion of the spring wire (3) is configured with an enlarged part (3*a*) for releasable location in a larger diameter proximal recess (10) in the handle member (1), the larger diameter proximal recess (10) being in fluid communication with one of the elongate recess (7) and the elongate passage (11) in the handle member (1), the larger diameter proximal recess (10) having a diameter that is larger than a diameter of one of the elongate recess (7) and the elongate passage (11) of the handle member (1).

17. Flexible surgical screw driver according to claim 11, wherein the shaft member (2) comprises an integral part which is configured with a recess (12), which tapers towards a distal portion of the shaft member (2) and into the passage (13) in the shaft member (2), and the passage (13) in the shaft member (2) for the spring wire (3).

18. Flexible surgical screw driver according to claim 1, wherein the elastically deformable spring wire (3) is made of a metallic material, of a plastic material, or of carbon fiber.

19. Flexible surgical screw driver according to claim 1, wherein the elastically deformable spring wire (3) extends through one of the elongate recess (7) and the elongate passage (11) in the handle member (1), the first coupling means (4) of the handle member (1), the passage (13) in the shaft member (2) and the second coupling means of the shaft member (2).

20. Flexible surgical screw driver according to claim 1, wherein the internal flexible m mbcr elastically deformable spring wire (3) is housed within the handle and shaft members (1, 2).

* * * * *